United States Patent [19]

Wyatt et al.

[11] Patent Number: 5,006,122
[45] Date of Patent: Apr. 9, 1991

[54] TISSUE TRANSPLANTATION SYSTEM

[75] Inventors: Richard J. Wyatt, Washington, D.C.; William J. Freed, Ft. Washington; Richard A. Staub, Waldorf, both of Md.

[73] Assignee: The United States of America as represented by the Department of Health and Human Services, Washington, D.C.

[21] Appl. No.: 588,242

[22] Filed: Sep. 20, 1990

Related U.S. Application Data

[63] Continuation of Ser. No. 278,821, Dec. 2, 1988.

[51] Int. Cl.$^5$ .............................................. A61M 5/178
[52] U.S. Cl. ............................ 606/130; 128/DIG. 26; 128/754; 604/158; 604/164
[58] Field of Search ............... 604/158, 164, 165, 166, 604/116, 174; 600/7, 8; 606/130, 185, 186, 129; 128/657, 791, 749, 751, 754, DIG. 26; 269/328

[56] References Cited

U.S. PATENT DOCUMENTS

| | | |
|---|---|---|
| 3,357,431 | 12/1967 | Newell ................................. 606/130 |
| 3,406,635 | 7/1963 | May ..................................... 604/164 |
| 4,386,602 | 6/1983 | Shelden et al. ...................... 606/130 |
| 4,581,019 | 4/1986 | Lurela ................................... 604/164 |
| 4,653,509 | 3/1987 | Oloff et al. ........................... 606/130 |
| 4,686,997 | 8/1987 | Oloff et al. ........................... 128/744 |
| 4,840,617 | 6/1989 | Osterholm .................... 128/DIG. 26 |

Primary Examiner—C. Fred Rosenbaum
Assistant Examiner—Kathleen A. Daley
Attorney, Agent, or Firm—Lowe, Price, LeBlanc, Becker & Shur

[57] ABSTRACT

The transplantation of donor tissue into the brain is effected by locking the head relative to a stereotaxic unit; penetrating the brain with a first cannula to a predetermined depth to create a transplant site within the brain while the first cannula is fixed by the stereotaxic unit relative to the brain; then feeding a second cannula, which contains donor tissue at its distal end, through the already fixed first cannula so that the distal end of the second cannula comes to rest at the transplant site; and finally withdrawing the first cannula and the second cannula so as to leave the donor tissue at the transplant site.

6 Claims, 3 Drawing Sheets

TISSUE TRANSPLANTATION SYSTEM

This application is a continuation application of application Ser. No. 07/278,821, filed Dec. 2, 1988 still pending.

FIELD OF THE INVENTION

The present invention relates to the transplantation of tissue, and more particularly to a method and apparatus for transplanting tissue into the brain with minimal damage to the brain and minimal disruption of the transplanted tissue.

BACKGROUND OF THE INVENTION

Transplantation of tissue into the mammalian central nervous system has become a widely used technique for exploring brain plasticity and developmental (Freed et al., 1985). Recent studies suggest that brain grafting may also have clinical utility (Madrazo et al., 1987). In the rat, the animal where most grafting research has taken place, grafts can be implanted using simple stereotaxically controlled injections (Perlow et al., 1979). This approach is very effective for implantation of tissues in the ventricles (Freed et al., 1981) or for implantation of dissociated cells (Bjorklund et al., 1980). Other procedures are available for placing grafts into the ventricular wall (Morihisa et al., 1984; Madrazo et al., 1987). When larger tissue fragments are implanted into the brain parenchyma, however, it becomes necessary to force the tissue into place by injecting substantial volumes under sufficient pressure to displace host brain tissue. This procedure may, therefore, alter the graft implantation site or even damage the grafted tissues.

Implantation of solid tissue fragments into brain parenchyma has often been relatively ineffective (Freed et al., 1986) for several reasons. For example, squirting or pushing tissue through a long needle may disrupt or damage the tissue. On the other hand, placing tissue into the brain with a spring or other holding device, which has been done with parkinsonian patients, presents potential problems associated with leaving a foreign object in the brain and may cause excessive disruption of host tissue (Backlund et al., 1985a,b). Direct visual placement, another approach to human work, is possible in only a limited number of brain sites (Morihisa et al., 1984; Madrazo et al., 1987); and in larger brains, such as those of monkeys and humans, these problems become more pronounced.

OBJECTS AND SUMMARY OF THE INVENTION

It is an object of the invention to overcome deficiencies in the prior art, as indicated above.

Another object of the invention is to provide for the improved transplantation of tissue into live brains.

It is a further object of the present invention to provide a brain tissue transplantation apparatus and method which will overcome the drawbacks and disadvantages of known transplant devices and methods.

Yet another object of the invention is to provide a method and apparatus for precisely locating a transplant site in the brain of the mammal, penetrating the brain to a predetermined depth to define the transplant site, and effecting the precise placement of donor tissue into the brain at the transplant site, while minimizing trauma or damage to the donor tissue and the recipient brain tissue.

Still another object is to provide a system of cannulas and inserts adaptable for use with and manipulation by conventional stereotaxic apparatus, which system facilitates the formation of a tissue transplant site in a mammalian brain and the subsequent deposition of donor tissue at the transplant site with minimal tissue trauma.

Still a further object is to provide a cannula assembly having at one end thereof an adjustable volume tissue retention chamber for receiving and retaining a predetermined amount of donor tissue, which will be subsequently deposited at a transplant site within a mammalian brain, and an adjustment mechanism at an opposite end of the cannula assembly for effecting variations in the retention chamber volume so that different amounts of donor tissue can be received and retained at different times.

These and other objects are accomplished by the use of tissue transplant apparatus for transplanting donor tissue from a source to a transplant site within a recipient brain. The tissue transplant apparatus includes a cannula and insert system including a first cannula assembly and a second cannula assembly, the first and second assemblies being adaptable for attachment to and manipulation by stereotaxic apparatus. The first cannula assembly includes a first guide cannula and a stylet or occluder, the latter being used for initial penetration only, after which it is removed. The second cannula assembly includes a second cannula and a second stylet, which together define an adjustable volume tissue retention chamber at one end of the second assembly. After donor tissue has been supplied to the retention chamber, the second cannula assembly is inserted into the first guide cannula so that the retention chamber is positioned, within the first guide cannula, in proximity to the transplant site. The donor tissue is deposited at the transplant site by lifting the inner and outer cannulas while maintaining the second stylet in a fixed vertical position relative to the transplant site.

Further objects, features and advantages of the present invention will be apparent from the following detailed description of embodiments taken in conjunction with the drawings.

BRIEF DESCRIPTION OF THE DRAWINGS

FIG. 2C shows an inner cannula and FIG. 2D shows a stylet insertable within the inner cannula of FIG. 2C;

DETAILED DESCRIPTION OF THE PREFERRED EMBODIMENTS

Figure 1:
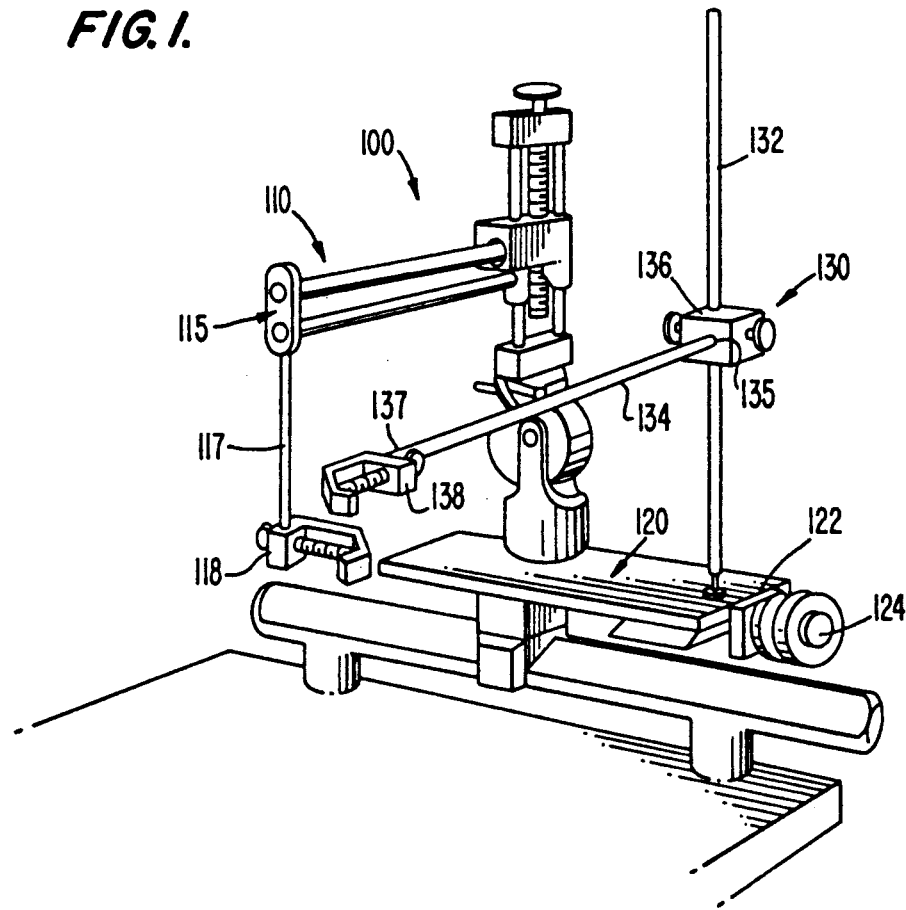
FIG. 1 is a perspective view of a stereotaxic apparatus modified for accepting the tissue transplantation apparatus of the present invention.

Referring now to the various Figures of the drawings, in which like or similar reference numerals represent like or similar elements, there is shown a tissue implantation apparatus of the present invention. FIG. 1 illustrates a known stereotaxic apparatus 100 (Model 1404 available from David Kopf Instruments, Tujunga, Calif.) which has been modified for use with the implantation apparatus (described in detail below) of the present invention. It is to be understood that the apparatus shown in FIG. 1 is only one example of a suitable stereotaxic device suited for use with the implantation apparatus of the present invention, and it is further contemplated that appropriate modifications of other stereotaxic devices for accepting the implantation apparatus are within the scope of skill of the ordinary artisan. Stereotaxic apparatus 100 includes a first carrier 110 (Model 1460 available from David Kopf Instruments, Tujunga, Calif.) mounted on a lateral slide base 120 (Model 1262, available from David Kopf Instruments, Tujunga, Calif.), which is modified to support a second carrier 130.

The modification is made by providing a drilled hole at an end 122 of the base 120 remote from the first carrier 110 and in the vicinity of adjustment knob 124. The second carrier 130 includes a vertical post 132, which is preferably a 7 mm diameter×25 cm long stainless steel support post, and a horizontal support rod 134, which is preferably a 7 mm diameter×10 cm long stainless steel element. One end 135 of rod 134 is connected to vertical post 132 by a 90° clamp block 136, while the opposite end 137 of rod 134 is attached to a universal clamp-type holder 138. A universal clamp-type holder 118 is also provided on the free end of vertical rod 117, the latter being suspended from the horizontal rod assembly 115 of the first carrier 110.

The tissue implantation apparatus of the present invention further includes first and second cannula assemblies and a holder assembly, as depicted in FIGS. 2A-2B, FIGS. 2C-2D and FIG. 2E, respectively.

Figures 2A, 2B, 2C, 2D, 2E:
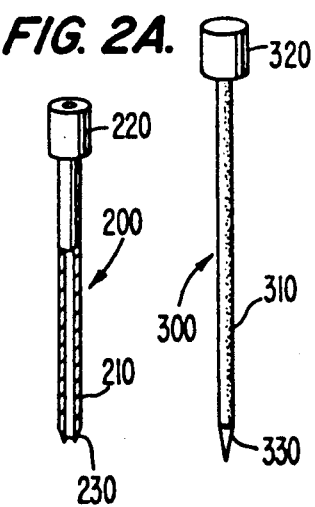
FIGS. 2A and 2B illustrate a first cannula assembly used to perform a first step in the method of tissue transplantation according to the present invention, FIG. 2A showing an outer guide cannula and FIG. 2B showing a stylet insertable within the outer guide cannula of FIG. 2A.
FIGS. 2C and 2D illustrate a second cannula assembly used in conjunction with the guide cannula of FIG. 2A to perform a further step in the method of tissue implantation according to the present invention, where
FIG. 2E illustrates a holder assembly for use with the second cannula assembly in performing a step of the method according to the invention.
Figure 3A:
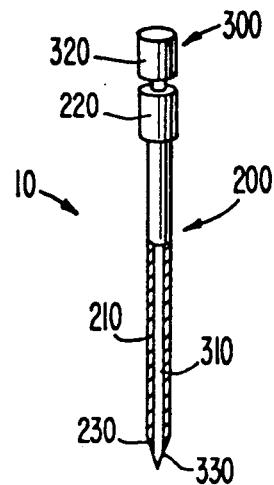
FIG. 3A shows the cannula assembly of FIGS. 2A and 2B and illustrates the stylet of FIG. 2A disposed within the cannula of FIG. 2B.

Referring to FIGS. 2A, 2B, and 3A, the first cannula assembly 10 is employed for making initial penetrations into brain tissue during surgery, and includes an outer guide cannula 200 and a first stylet or occluder 300 interfitted within the cannula 200. Cannula 200 includes a tube 210 and a tubular cap 220 having a bore of a diameter adapted to snuggly receive one end of tube 210 and which is secured to the one end of tube 210 by a soldered connection or the like. The other end of tube 210 distal from cap 220 is beveled to form a cutting edge 230. Desirably the tube 310 is 94 mm long and has a wall thickness of 0.23 mm, an outer diameter of 1.651 mm and an inner diameter of 1.193 mm; and the tubular cap 220 is 10 mm long and 8 mm in diameter. Stylet 300 includes a solid rod member 310 preferably made of stainless steel having one end region secured by solder or the like within a bore drilled in a solid brass cap 320, and having its opposite end region 330 sharpened to provide a penetration bevel at the same angle as the bevel 230. In the preferred embodiment of stylet 300, the rod member 310 has a length of about 105 mm and an outer diameter of about 1.066 mm, while the cap 320 is about 10 mm long and about 8 mm in outer diameter.

The second cannula assembly 20, which is employed along with cannula 200 for effecting tissue transplantation during surgery (as described below in greater detail), includes a second cannula 400 (FIG. 2C) and a second stylet or occluder 500 (FIG. 2D), and holder assembly 600 (FIG. 2E).

Cannula 400 includes a tube 410 having an outer wall milled slightly to fit within tube 210 of cannula 200, and a cap 420 secured at one end of the tube 410 by a solder connection made in a manner similar to the soldered connection of cap 220 to tube 210 of cannula 200. The end of tube 410 remote from cap 420 is beveled to provide a sharpened cutting edge 430 suitable for punching into tissue to be transplanted. The preferred embodiment of the cannula 400 which is adapted for use on monkeys has a length of about 104 mm, with the tube 410 having an inside diameter of about 0.685 mm, an outside diameter of about 1.066 mm and a wall thickness of abut 0.177 mm. The preferred embodiment of the cap 420 has an outer diameter of 8 mm and a length of 10 mm. Stylet 500 is similar to stylet 300 in construction; however, in the preferred embodiment of the invention, the outside diameter of rod 510 is about 0.558 mm and the overall length of the stylet 500 including cap 520 is about 115 mm. The distal end 530 of the stylet 500 is desirably blunt rather than tapered or pointed.

Holder assembly 600, shown in FIG. 2E, is used with cannula 400 and stylet 500 for determining the amount of tissue to be transplanted, and for assisting in the precise deposition of the donor tissue in the brain at the transplant site (to be described in greater detail below).

As shown, the holder assembly 600 includes a tubular shell 610 into which the caps 520, 420 of stylet 500 and cannula 400, respectively, are inserted. At one side of the tubular shell 610 is a viewing slot 620 by which a surgeon can determine the relative distance between the caps 520 and 420 of the stylet 500 and the cannula 400, and hence by direct correspondence the relative distance between the free ends 530, 430 of the stylet 500 and cannula 400 (the purpose of which is described below).

A grouping 630 of graduation marks or lines, i.e. a linear scale, is located adjacent one side of viewing slot 620. The lines in grouping 630 are spaced apart by predetermined distances (in the preferred embodiment, the lines are spaced apart from one another by about 1 mm). A set screw 640 is provided at the upper end region of the tubular shell 610 for securing therein the cap 520 of stylet 500. A thumb screw 650, provided at the lower end region of the tubular shell 610, is coupled with and permits selective tightening or loosening of a clamp member 660 disposed within the shell so that end cap 420 of cannula 400 can be adjustably positioned, and secured within shell 610, at a desired location relative to the stylet end cap 520. A rod-like protrusion 670, located at the upper end of shell 610 is adapted to be tightly gripped by holder 138 of the second carrier 130 supported on the stereotaxic apparatus 100 shown in FIG. 1.

The method of tissue transplantation according to the present invention involves essentially three steps:
(1) first, locating the transplant site and effecting a desired depth of penetration into the receiving brain tissue to reach the transplant site, using the first cannula assembly clamped in the stereotaxic apparatus;
(2) second, determination of the amount of tissue to be transplanted and obtaining the determined amount, using the second cannula assembly; and
(3) third, depositing the determined amount of tissue into the brain at the transplant site, using the second cannula assembly received in the bore of the first cannula 200.

Figure 3B:
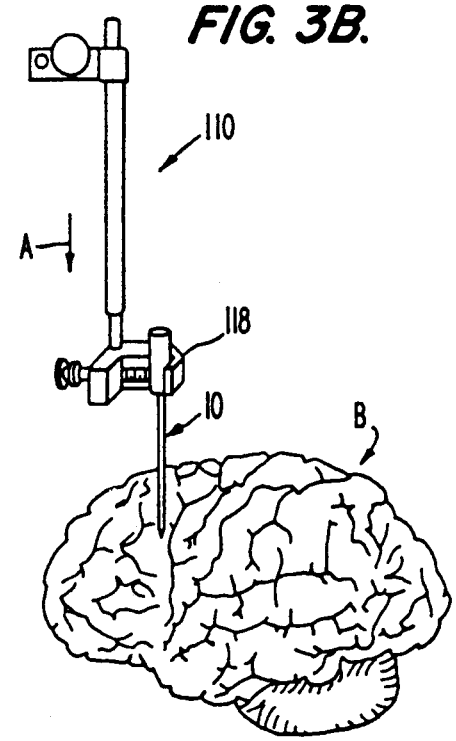
FIG. 3B illustrates the use of a first carrier of the stereotaxic apparatus of FIG. 1 with the first cannula assembly of FIGS. 2A and 2B for initially locating the position in a brain where the tissue will be implanted.

During surgery, e.g. for research purposes in laboratory mammals or in the therapy of humans suffering from Parkinson's disease, initial penetrations into the brain B (see FIG. 3B) are effected through the use of the first cannula assembly 10 and the first carrier 110 of the stereotaxic apparatus 100 shown in FIG. 1. Specifically, after the transplant site has been identified and a skull opening has been provided to gain access to the transplant site, the first cannula assembly 10 is secured to the first carrier 110, via holder 118, and positioned at the skull opening by appropriate manipulations of the controls of stereotaxic apparatus 100. First carrier 110 is then moved vertically in the direction of arrow A until a desired penetration depth is reached by the distal end 230/330 the first cannula assembly 10. Thereafter, while cannula 200 is maintained in place at the penetration depth by first carrier 110, the stylet 300 is removed, the cannula 200 remaining in place within the brain.

Preliminary to or following the initial penetration into the brain B of the first cannula assembly 10, the second cannula assembly 20 is used to determine an amount of donor tissue to be transplanted, and to obtain and hold ready that determined amount of tissue until the step of deposition of the tissue is to be carried out.

Figure 4A:
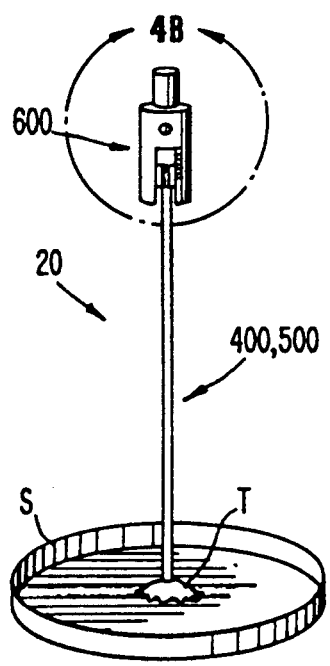
FIG. 4A illustrates the attachment of the holder assembly of FIG. 2E to the second cannula assembly of FIGS. 2C and 2D for the purpose of punching donor tissue prior to its implantation in the brain.
Figure 4B:
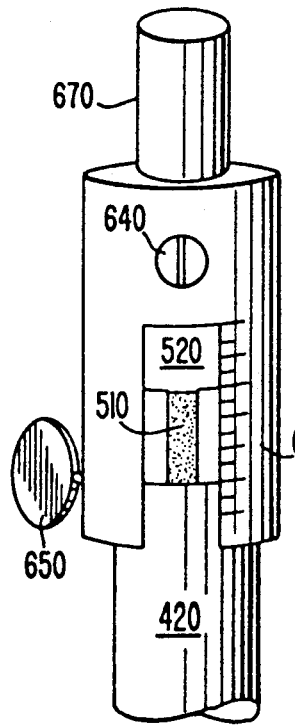
FIG. 4B is an enlarged view of the holder assembly shown in FIGS. 2E and 4A, and illustrating the manner of determining the amount of donor tissue to be retained for transplantation.
Figure 4C:
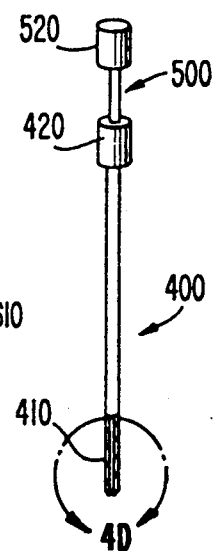
FIG. 4C shows the relative positions of the cannula and stylet of the second cannula assembly after the donor tissue has been retained.

Referring first to FIGS. 4A and 4C, the second cannula assembly 20 includes cannula 400, stylet 500 disposed concentrically within the 410 of cannula 400 (shown in FIG. 4C) and holder assembly 600. As seen in FIG. 4A, the second cannula assembly 20 is used for the purpose of obtaining, e.g. by punching or cutting from a suitable source S an amount of donor tissue T. In order to accomplish this task, it is first necessary to determine the quantitative volumetric amount of tissue T which must be obtained from the Source and held within the cannula 400 of the second cannula assembly 20.

Figure 4D:
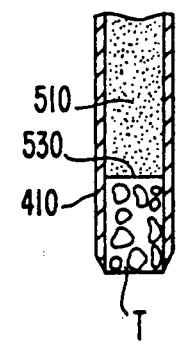
FIG. 4D is an enlarged view of the lower region of the cannula assembly of FIG. 4C, showing the manner in which donor tissue is retained.

Referring now to FIG. 4B, once the selected volumetric amount of tissue T has been determined, it is merely a matter of moving the cannula end cap 420 away from the end cap 520 of the stylet 500 a linear distance within the tubular shell 610 of holder assembly 600. Such a distance is directly proportional to the volume at the lower end of tube 410 which is unoccupied by the stylet rod 510. By using the viewing slot 620 and the grouping 630 of lines adjacent the slot 620 after thumb screw 650 and clamp 660 are loosened, an appropriate adjustment of the spacing between end cap 520 and end cap 420 can be made. Thereafter, thumb screw 650 is turned back so as to retighten clamp 660 about the end cap 420 to secure the latter in place relative to the end cap 520. FIG. 4D illustrates the relative positioning between the lower end 530 of the rod of the stylet 500 and the lower end of the tube 410 of the cannula 400 in order to accommodate a predetermined amount of tissue T.

As illustrated in FIG. 4D, the selected volume of tissue T is captured or retained within the lower end of the tube T.

Figure 5A:
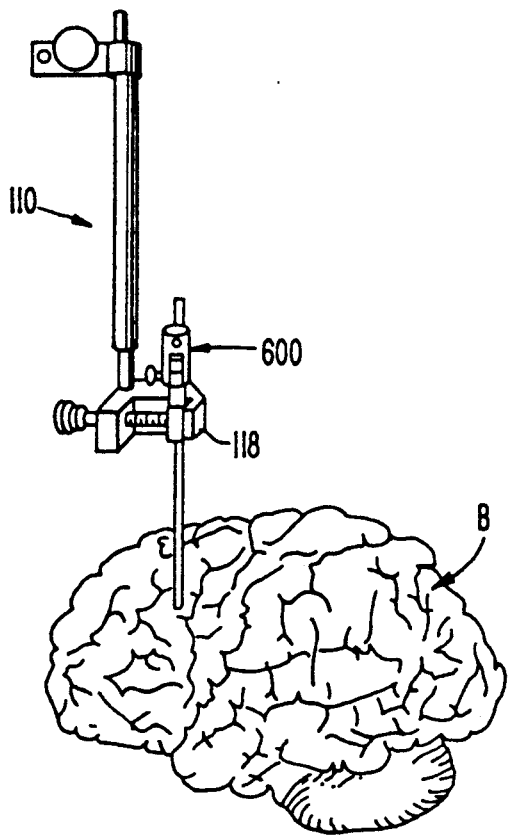
FIG. 5A illustrates the use of the stereotaxic apparatus prior to implantation of the donor tissue in the brain.
Figure 5B:
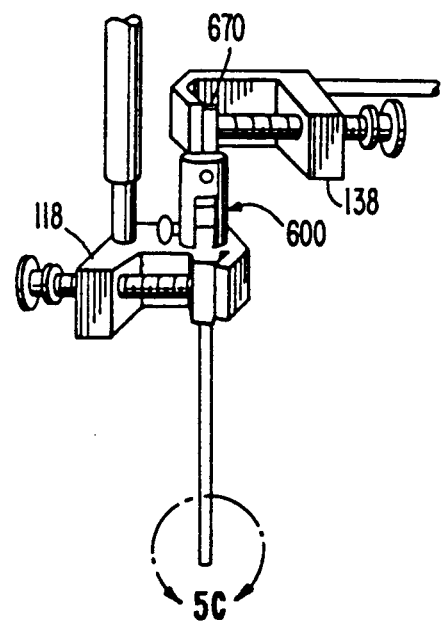
FIG. 5B shows the manner of attachment of the guide cannula of FIG. 2A and the second cannula assembly of FIGS. 2C and 2D to the stereotaxic apparatus prior to brain tissue implantation.
Figure 5C:
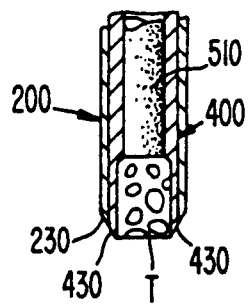
FIG. 5C is an enlarged view of the lower region of the guide cannula and second cannula assembly in FIG. 5B and showing the relative positions of the cannula components, stylet and donor tissue.

Following the filling of the second cannula assembly 20 with the selected quantity of tissue T, the second cannula assembly 20 is inserted into the outer guide cannula 210 of the first cannula assembly 10 (see FIG. 5A), and the rod-like protrusion 670 top holder assembly 600 is affixed to clamp 138 of the stereotaxic apparatus, second carrier 130 (see FIG. 5B). In this "piggyback" position, the lower end 230 of the cannula 200 is disposed slightly above the lower end 430 of cannula 400 (as shown in FIG. 5C) so that the lower ends of cannulas 200 and 400 exhibit one continuous bevelled surface.

Figure 5D:
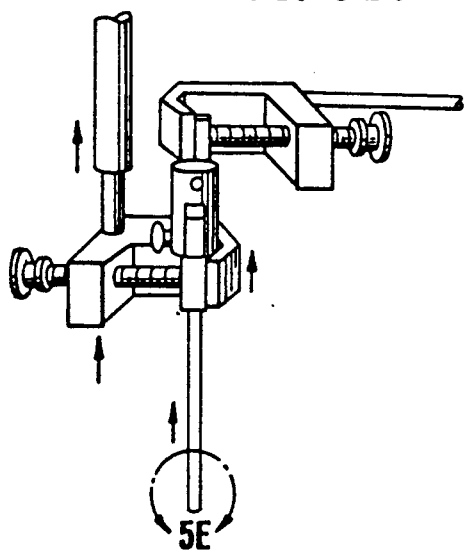
FIG. 5D illustrates the intended manner of using the stereotaxic apparatus to effect the implantation of donor tissue into the brain.
Figure 5E:
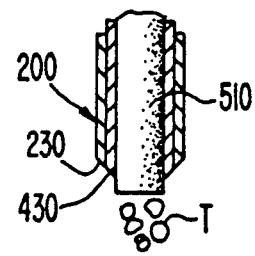
FIG. 5E is an enlarged view of the lower end of the cannula shown in FIG. 5D illustrating the manner in which the donor tissue is released at the transplantation site.

Referring now to FIGS. 5D and 5E, after the first and second carriers 110 and 130 of the stereotaxic apparatus are attached to end cap 220 and protrusion 670, the thumb screw 650 is turned so that clamp 660 is loosened. Then, the first carrier 110 is raised vertically relative to the second carrier 130 so that the tube 210 rides over the exterior surface of tube 410 until the end cap 220 of the cannula 200 abuts the end cap 420 of cannula 400. Thereafter, further vertical movement upwardly of the first carrier 110 relative to the second carrier 130 causes end cap 420 (and hence cannula 400 of the second cannula assembly 20) to move upwardly relative to and toward the end cap 520 of stylet 500. As the cannula 400 is raised in this manner, the separation between end caps 420 an 520 is visibly seen to diminish via viewing slot 620 and the tissue T held in the lower tubular region of cannula 400 is gradually and gently released into the transplant site.

The foregoing discussion of the manner of effecting tissue transplantation according to the present invention relates to tissue transplants at single sites as well as tissue transplants at multiple sites. The latter is accomplished by disconnecting the second carrier 130 from the holder assembly 600, lifting the first carrier 110 so that the "piggy-backed" cannulas 200, 400 are removed from the initial transplant site, and repeating the aforedescribed three step transplant procedure at a newly selected or defined transplant site.

The preferred dimensions as indicated above are selected on the basis of experiments which have shown that the cross sectional size of cannula 400 as noted above, i.e. 0.685 mm, is the smallest that can be used to reliably punch adrenal medulla from the monkey, Macaca mulatta. Dimensions of the other cannula and stylets are determined by cannula 400. For use on humans, it is preferred that the maximum outer diameter of the tube 210 be no greater than 1.0 mm.

Preliminary data indicate that the present device is superior to other techniques for transplantation of adrenal medulla into the primate striatum. In a number of sites, tens of thousands of cells have survived while in other sites only a few cells survived. While the number of surviving cells is inconsistent, the tissue transplantation apparatus of the present invention affords better maximum survival of adrenal chromaffin cells than other techniques which have been used in monkeys. The survival of cells using the method and apparatus of the invention is also superior to others known and/or practised for the parenchyma of the rat brain—where about 200 chromaffin cells per animal survive permanently when stereotaxically injected into the striatum in a fluid vehicle (Freed et al., 1986), or when transplanted by simply forcing the tissue from the needle with a stylet (Freed, unpublished data).

In summary, there has been described an apparatus and method for inserting brain tissue into the mammalian brain with minimal pressure and minimal disruption of the transplanted tissue. The transplantation apparatus can be easily guided to the transplantation site with a stereotaxic instrument, and it can be used for placing tissue into multiple sites along a single tract, or for placing tissue, when necessary, along multiple tracts. The brain tissue transplanter or grafter can be manufactured from readily available materials and its dimensions altered for animals with different sized brains.

The brain tissue transplanter or grafter can be used not only with Macaca mulatta adrenal medulla, which is fairly fibrous and holds together well as a piece, but also for embryonic brain tissue, which is much more fragile and therefore more difficult to manipulate and insert without damage.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. Apparatus for transplanting tissue into a brain, comprising:

first tubular cannula means for penetrating a brain to a predetermined depth to form a transplant site;

second tubular cannula means for releasably holding said tissue to be transplanted, said second cannula means including a portion at one end thereof of reducible volume, said portion being adapted to obtain and hold a predetermined quantity of donor tissue;

first mechanical support means for releasably receiving and maintaining said first cannula means at said predetermined depth within the brain while said second cannula means is inserted into said first cannula means to such an extent that the tissue-filled portion of the second cannula means is located in the vicinity of said transplant site;

second mechanical support means for releasably receiving and maintaining said second cannula means fixed in position relative to said transplant site following insertion of said second cannula means into said first cannula means;

mechanical means for moving said first cannula means relative to said second cannula means and in a direction away from said transplant site;

whereby movement of said first cannula means relative to said transplant site in said direction causes a reduction in volume of said reducible volume portion such that the tissue held in said second cannula means is released and deposited at said transplant site.

2. The apparatus of claim 1, wherein said first and second mechanical support means, and said means for moving said first cannula means relative to said second cannula comprise components of a stereotaxic apparatus.

3. Apparatus for transplanting tissue into a brain comprising:

a first cannula means for penetrating a brain to a predetermined depth to form a transplant site, said first cannula means comprising a first elongated tube having an axial bore therethrough;

a second cannula means for releasably holding tissue to be transplanted, said second cannula means having a distal end portion of reducible volume, said distal end portion being capable of holding a predetermined quantity of donor tissue;

first mechanical support means for releasably receiving and holding said first cannula means during penetration of the brain and for maintaining said first cannula means at said predetermined depth within the brain while said second cannula means is inserted into the bore of said first cannula means such that the distal end portion of the second cannula means becomes located in the vicinity of said transplant site;

second mechanical support means for releasably receiving and maintaining said second cannula means fixed in position relative to said transplant site following insertion of said second cannula means into said first cannula means, and for maintaining said second cannula means fixed while withdrawing said first cannula means; and means for depositing donor tissue from said distal end portion of said second cannula means at said transplant site.

4. Apparatus according to claim 3 wherein said first cannula means further comprises a first elongated stylet slidably received within said first elongated tube, said first stylet having a pointed distal end.

5. Apparatus according to claim 3 wherein said second cannula means comprises a second elongated tube having a distal open end and an external diameter slightly less than the internal diameter of said first elongated tube of said first cannula means, and a second elongated stylet slidably received within said second elongated tube, said distal end portion of said second cannula means comprising a variable volume extending from the distal end of said second stylet to the distal end of said second elongated tube.

6. Apparatus according to claim 5 wherein said means for depositing donor tissue at said transplant site comprises means for controllably withdrawing said second elongated tube of said second cannula means in an axial direction relative to said second stylet.

* * * * *